US007151253B2

(12) United States Patent
Varchena et al.

(10) Patent No.: US 7,151,253 B2
(45) Date of Patent: Dec. 19, 2006

(54) DYNAMIC PHANTOM FOR RADIATION THERAPY

(76) Inventors: Vladmir Varchena, 2301 Catamaran Ct., Virginia Beach, VA (US) 23451; Mark T. Devlin, 621 Delaware Ave., Virginia Beach, VA (US) 23451; Moustafa Zerhouni, 4644 Truman La., Virginia Beach, VA (US) 23455; Terry W. Moore, 1816 Castelton Ct., Virginia Beach, VA (US) 23454

( * ) Notice: Subject to any disclaimer, the term of this patent is extended or adjusted under 35 U.S.C. 154(b) by 228 days.

(21) Appl. No.: 10/940,494

(22) Filed: Sep. 14, 2004

(65) Prior Publication Data

US 2005/0211889 A1 Sep. 29, 2005

Related U.S. Application Data

(60) Provisional application No. 60/556,640, filed on Mar. 26, 2004.

(51) Int. Cl.
*G12B 13/00* (2006.01)

(52) U.S. Cl. .................................................. 250/252.1

(58) Field of Classification Search .............. 250/252.1
See application file for complete search history.

(56) References Cited

U.S. PATENT DOCUMENTS 4,331,869 A * 5/1982 Rollo ...................... 250/252.1
4,538,071 A * 8/1985 Bardoux et al. ......... 250/505.1
4,613,754 A * 9/1986 Vinegar et al. .......... 250/252.1
5,236,363 A * 8/1993 Sandrik et al. ............. 434/267
6,225,622 B1 * 5/2001 Navarro ................... 250/252.1
6,697,451 B1 * 2/2004 Acharya et al. .............. 378/18
6,992,280 B1 * 1/2006 White et al. ............. 250/252.1
2004/0075048 A1 * 4/2004 Zyromski ................ 250/252.1
2005/0077459 A1 * 4/2005 Engler et al. ............ 250/252.1
2005/0139758 A1 * 6/2005 White et al. ............. 250/252.1
2005/0141672 A1 * 6/2005 Endo et al. ................. 378/207

* cited by examiner

*Primary Examiner*—David Porta
*Assistant Examiner*—Christopher Webb
(74) *Attorney, Agent, or Firm*—Stephen E. Clark

(57) ABSTRACT

The present invention is a thorax phantom that enables simulation of tumor motion within a tissue equivalent material. The system consists of a tissue equivalent epoxy phantom representing a 15 cm axial section of the human thorax that includes simplified spine and lung anatomies. Within the phantom are thru rods of similar tissue density. The rods are attached to a computer-controlled actuator that facilitates both linear and rotational motion of the rods within the phantom. A plurality of tumor targets and radiation detectors can be placed within the rods at various locations thereby enabling the simulation of respiratory and cardiac induced tumor motions within the phantom and assessment of the effects of these motions on image acquisitions, treatment planning and radiation treatment delivery.

20 Claims, 10 Drawing Sheets

100
22
20
21a
21b
33
34
35

Actuator with Supporting Adjustable Frame.

200
22
201
23
20
21

DYNAMIC PHANTOM FOR RADIATION THERAPY

CROSS REFERENCE TO RELATED APPLICATIONS

Inventors claim priority benefits of Provisional Patent Application Ser. No. 60/556,640 Filed on Mar. 26, 2004.

FIELD OF INVENTION

The present invention relates generally to diagnostic imaging and radiation therapy systems and more specifically to a method and apparatus for evaluation of said systems and their capability to correctly compensate for dynamic target motions in both image acquisitions, treatment planning and dose delivery situations, by providing a tissue equivalent phantom member having an operator controllable target member dynamically disposed within the phantom member.

BACKGROUND OF THE INVENTION

It is estimated that approximately 50% of all cancer patients will undergo some form of radiation therapy as part of their curative treatment. The objective of radiation therapy is to accurately focus lethal doses of ionizing radiation to cancer cells while minimizing dose to healthy tissues surrounding the cancer. Towards that end there have been many technological innovations over the years to improve the accuracy of radiation therapy including better patient immobilization devices, computerized treatment planning based on three dimensional CT and MRI images and precise beam shaping through such devices as the multi-leaf collimator. Advance treatment techniques such as Intensity Modulated Radiation Therapy (IMRT) have enabled treatment "safety margins" surrounding tumors or "planned treatment volumes" to be dramatically reduced. Tumor motion as a result of patient breathing or cardiac function in such areas as the lungs or mediastinum may compromise the accuracy of delivery.

One solution to this problem is to increase the treatment volumes to account for the target drift. Other techniques involve modeling the motion as part of the treatment plan and gating or synchronizing the delivery with the target motions.

There exists today a need to assess and measure the various methods being employed to correct for errors in dose delivery to dynamic targets.

Navarro U.S. Pat. No. 6,225,622 to Navarro discloses a dynamic radiation scanning device wherein the entire phantom, along with any embedded radiation detector, is moved as a whole to asses beam flatness and uniformity.

Another prior approach involves intermittently moving a detector to various positions through a water-filled tank, and taking still (i.e., non-moving) radiation dosage readings at each position. This prior approach does not contemplate continuous movement of the detector relative to a fixed medium, and taking dosage readings while the detector is moving.

U.S. Pat. No. 6,697,451 to Acharya et al discloses a dynamic phantom an method for evaluation of calcium scoring. In the Acharya et al device, the center section of a phantom is moved to mimic cardiac motion for CT scoring of coronary calcification. This prior device does not provide for insertion of a continuously moving detector within a target volume.

Yang et.al ("*An Investigation of tomotherapy beam delivery*", 1997, *Medical Physics*, American Association of Physics and Medicine) discloses a phantom positioning device wherein said device uses linear and rotational motions but to move an entire phantom linearly and rotationally as a whole, but does not disclose or teach movement of a target volume within the phantom.

Jiang et al ("*An experimental investigation on intra-fractional organ motion effects in lung IMRT treatements*", 2003, *Physics in Medicine and Biology*, Institute of Physics Publishing) disclose sinusoidal movement of an entire phantom and its surrounding structure, similar to Yang, but does not disclose or teach moving a target within a structure.

Hugo et al ("The effects of tumor motion on planning and delivery or respiratory-gated IMRT", 2003, Medical Physics, American Association of Physics and Medicine) disclose moving the entire phantom as with Yang and Jiang, and additionally discloses moving the phantom in a vertical and longitudinal direction simultaneously, but does not disclose or teach moving a target within a structure.

Sawada et al ("*A technique for noninvasive respiratory gated radiation treatment based on a real time 3D ultrasound image correlation: A phantom study*" 2004, *Medical Physics*, American Association of Physics and Medicine) disclose Targets embedded in a rubber cylinder that moves within a water tank simulating a human abdomen, for evaluation and development of 3D ultrasound system used to correct for respiratory tumor motions specific to the abdominal cavity. Sawada et al do not disclose or teach a thorax- or lung-simulating phantom, nor the provision of detectors within the target volume to assess dosage.

SUMMARY OF THE INVENTION

Stereotactic Body Radiation Therapy (SBRT) represents an exciting new development in the field of radiation therapy wherein large hypofractionated doses of radiation may be delivered conformally to targets of liver and lung. The delivery of large conformal doses to such targets poses numerous challenges, which can include the presence of significant degrees of target motion. According to the present invention a dynamic thorax phantom is constructed to allow for motion studies of targets in the lung. The dynamic thorax phantom is constructed from a thorax phantom, modified so as to allow for complex, unit-density target motion in lung equivalent material. Through a combination of translational and rotational motion, a motion actuator facilitates three-dimensional motion of the target volume within the thorax phantom. Means are provided by which linear motion in the superior/inferior (S/I) direction can be isolated from lateral and anterior/posterior (A/P) motion in both frequency and amplitude, and the two sets of motions may be synchronized to each other. Means are also provided by which sinusoidal and other complex motions of the target volume within the thorax volume are achievable. An embodiment of the phantom is designed specifically to facilitate study the ramifications of dynamic target motion in the lung, in the presence of temporally modulated radiation therapy delivery beams (i.e. IMRT). In accordance with the present invention, a dosimetric evaluation of target coverage can be generated for the specific cases of delivery via serial tomotherapeutic IMRT, static gantry IMRT and static field treatment.

These and other objects and advantages of this invention will become apparent from the following description taken in conjunction with the accompanying drawings wherein are set forth, by way of illustration and example, certain embodiments of the present invention.

LIST OF PART NUMBERS

Figure 1:
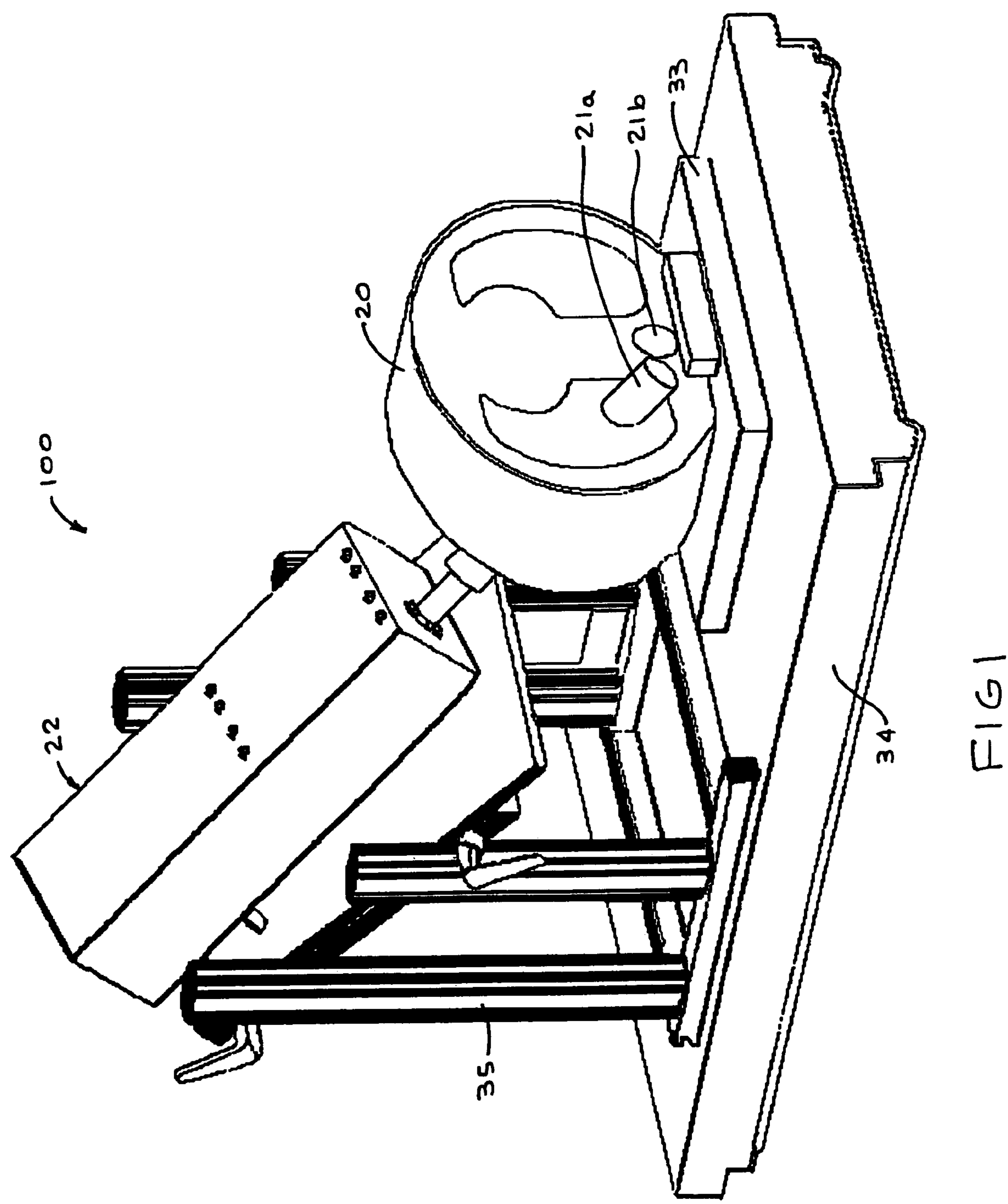
FIG. 1 is a perspective view of a dynamic phantom assembly for radiation therapy constructed in accordance with the present invention.
Figure 2:
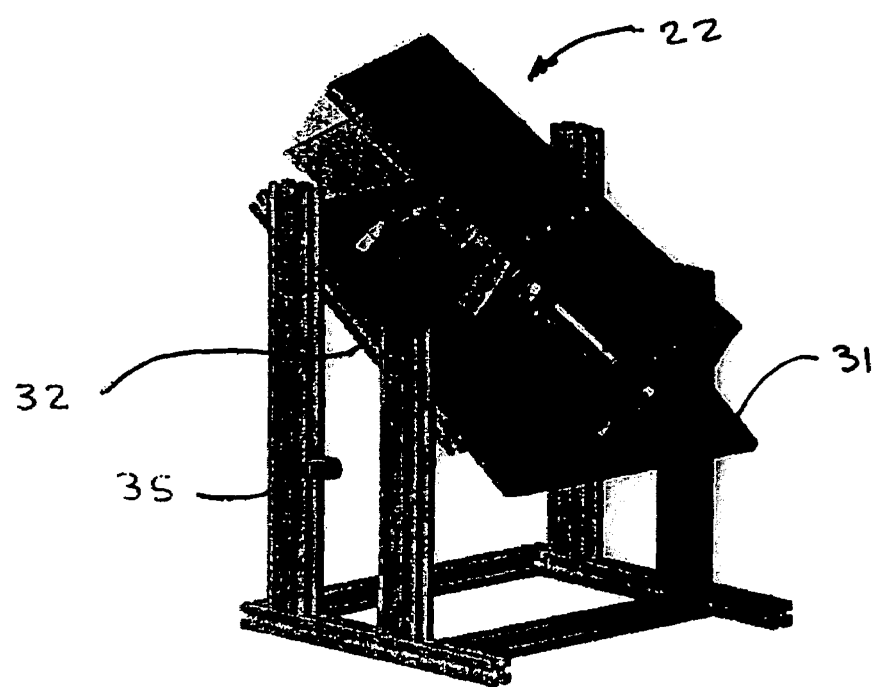
FIG. 2 is a perspective view showing the actuator and supporting adjustable frame of the dynamic phantom assembly of FIG. 1.
Figure 3:
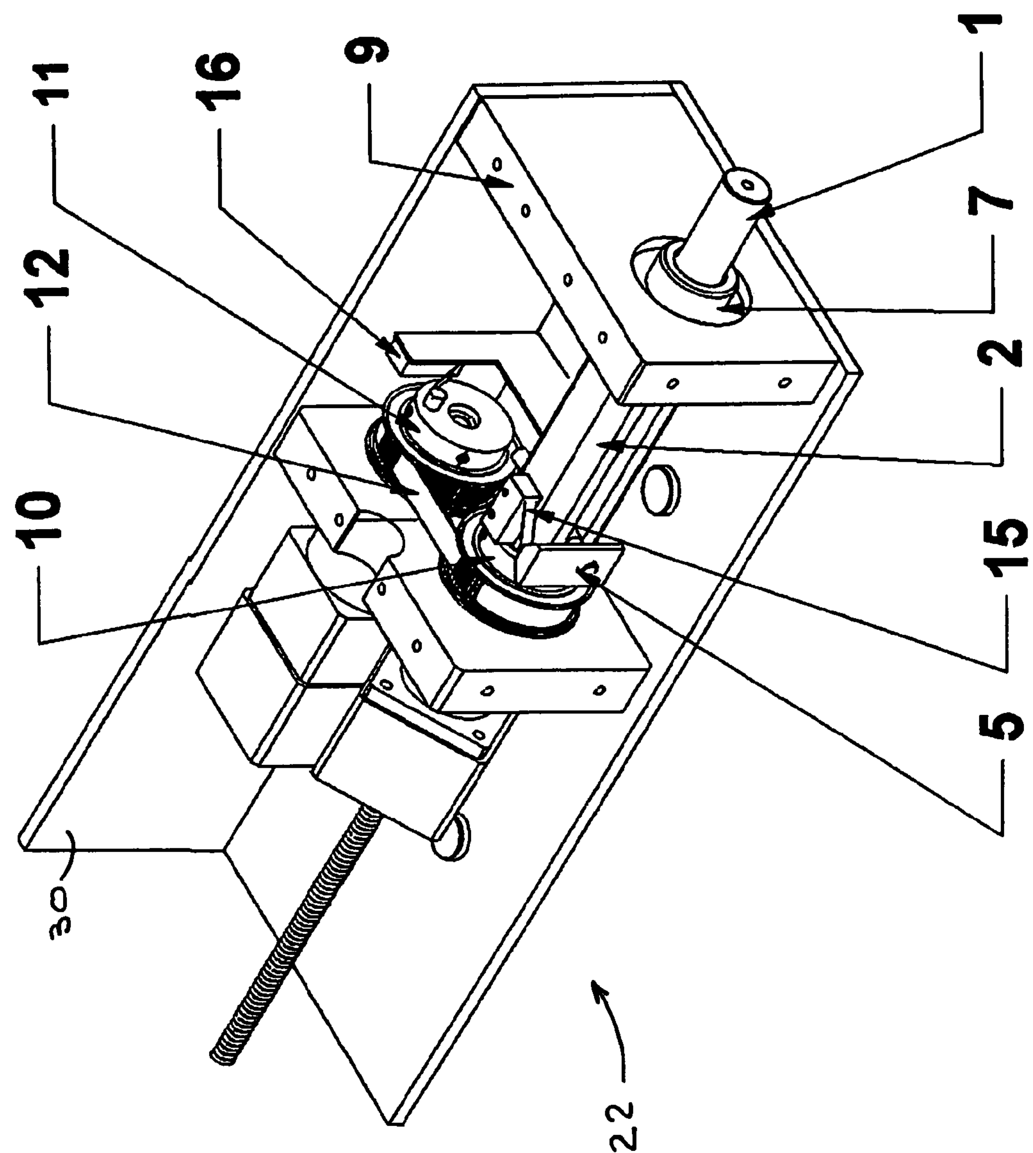
FIG. 3 is a perspective top view of the actuator of FIG. 2.
Figure 4:
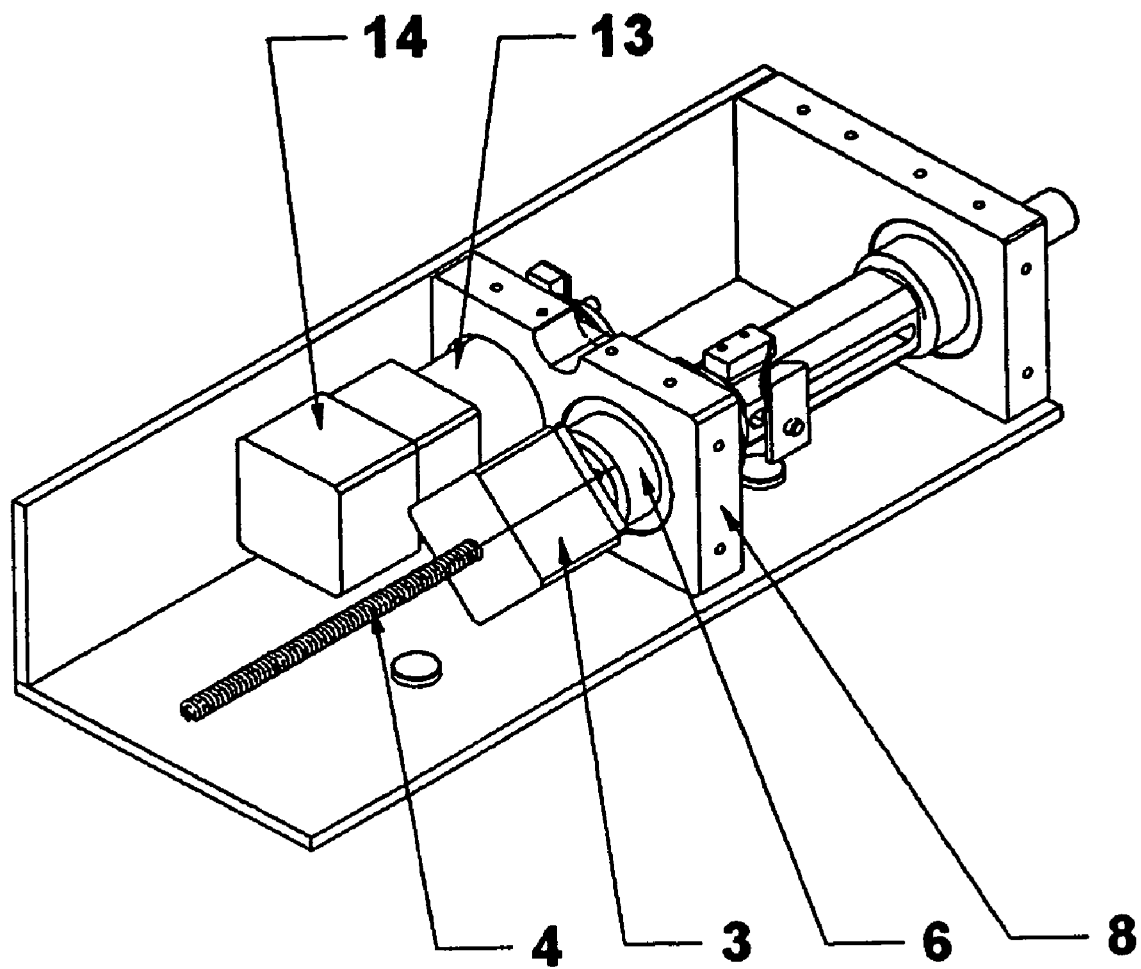
FIG. 4 is a perspective partial view showing details of construction of the actuator of FIG. 3.
Figure 5:
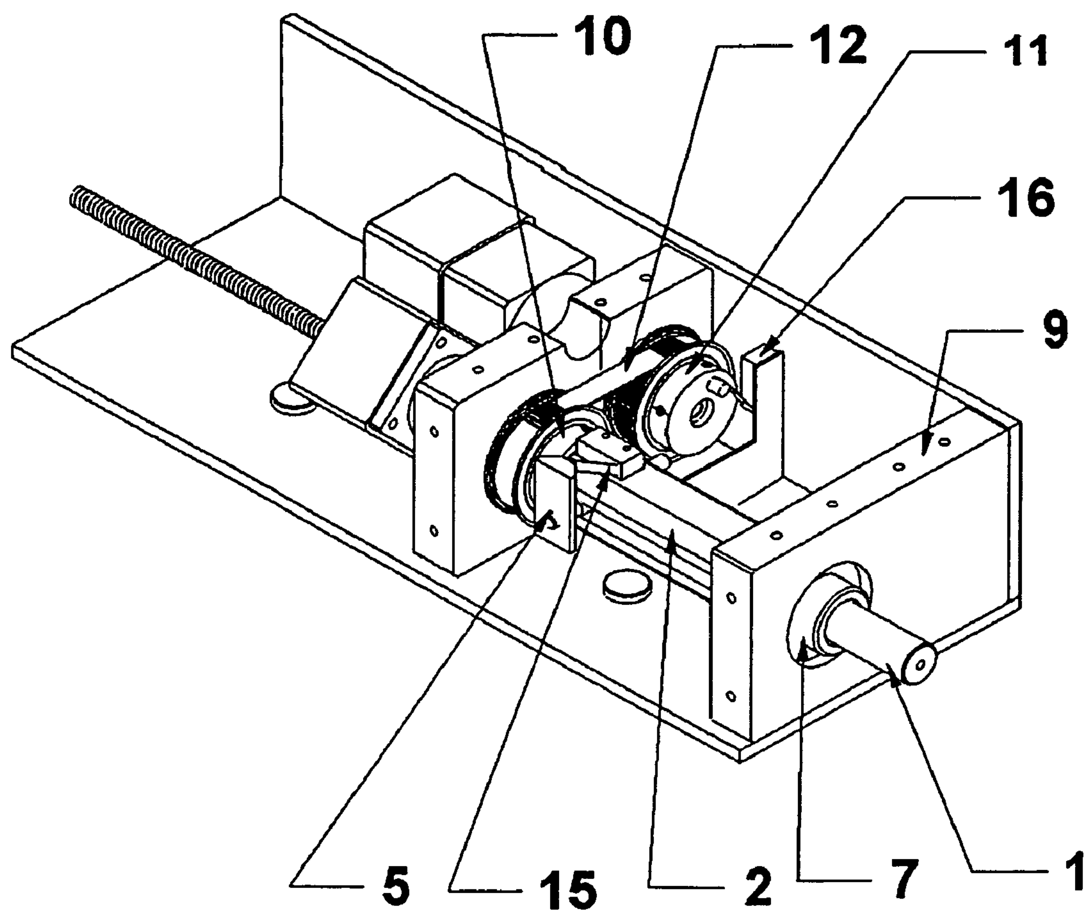
FIG. 5 is a perspective partial view showing details of construction of the actuator of FIG. 3.
Figures 6, 7:
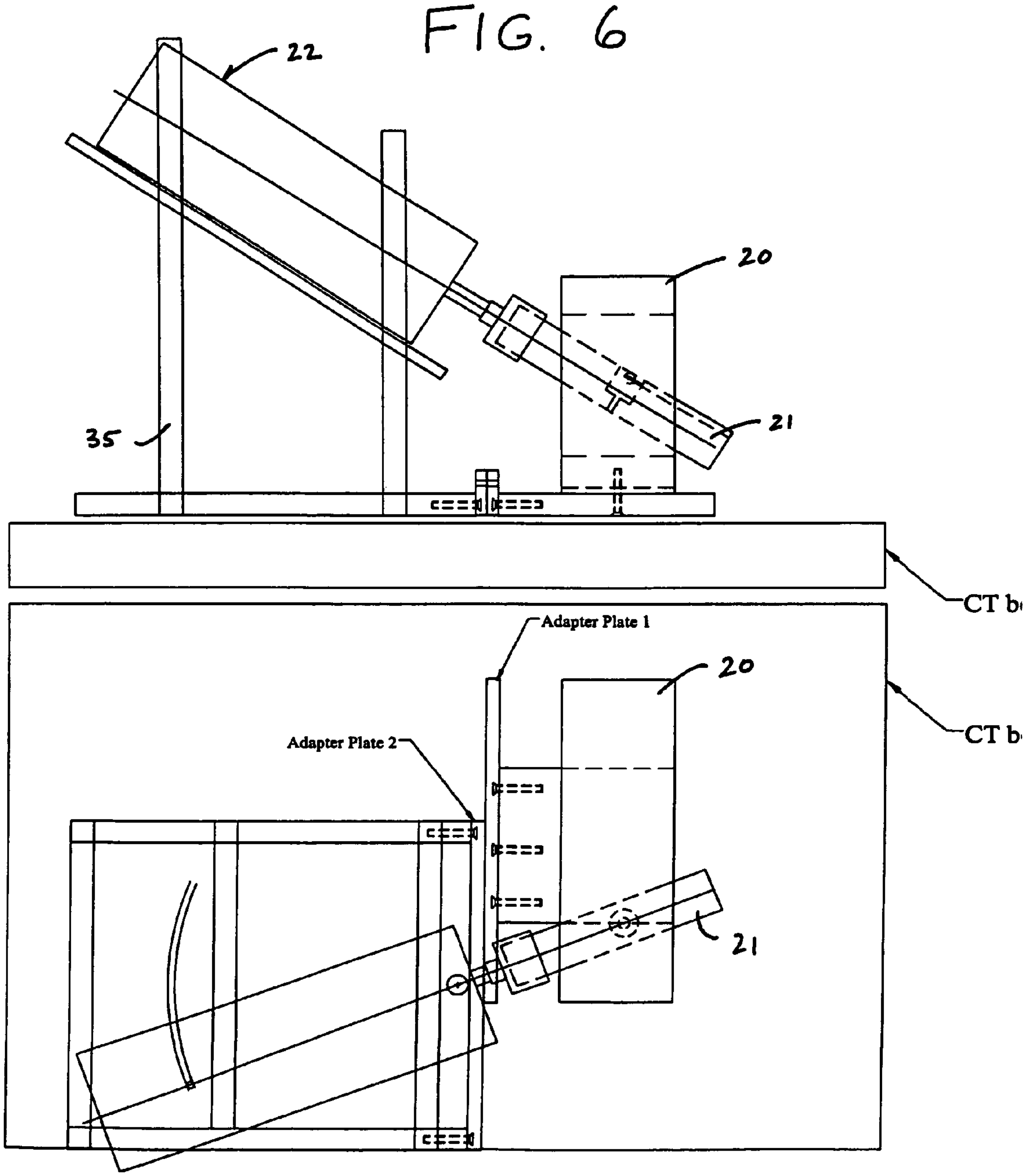
FIG. 6 is a side elevation view of a dynamic phantom assembly for radiation therapy constructed in accordance with the present invention.
FIG. 7 is a plan view of a dynamic phantom assembly for radiation therapy constructed in accordance with the present invention.
Figure 8:
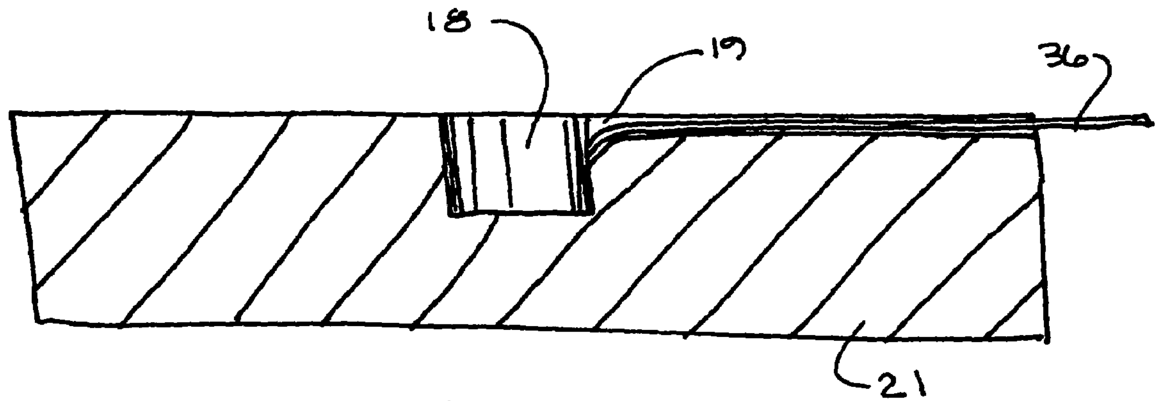
FIG. 8 is a longitudinal cross-sectional view of a tissue equivalent rod in accordance with the present invention.
Figure 9:
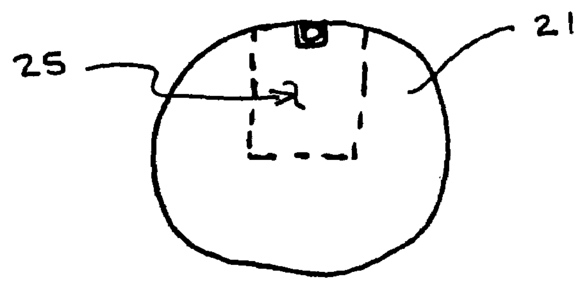
FIG. 9 is an elevation view of one end of the tissue equivalent rod of FIG. 8.
Figure 10:
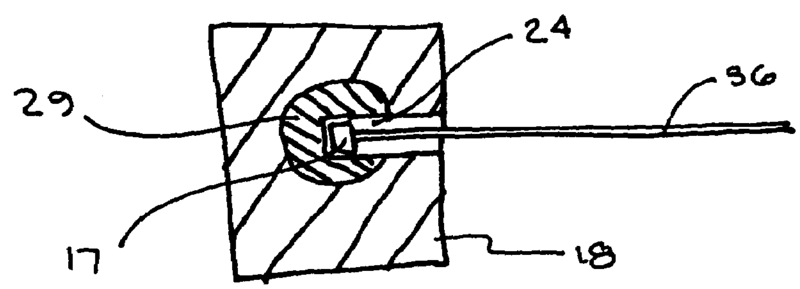
FIG. 10 is a medial cross-sectional view of a rod insert.

1 Actuator rod
2 Actuator cylinder
3 Stepper motor
4 Acme screw
5 Anti-rotation pin
6 Bearing
7 Bearing
8 Bearing plate
9 Bearing plate
10 Pulley
11 Pulley
12 Timing belt
13 Planetary gear-head
14 Stepper motor
15 Limit switch
16 Limit switch
17 Detector member
18 Rod insert
19 Groove in Tissue equivalent rod 21
20 Tissue equivalent phantom
21 Tissue equivalent rod
22 Actuator assembly
23 Motion controller assembly
24 Hole in Target volume
25 Hole in Tissue equivalent rod 21
26 Computer
27 First Hole through phantom
28 Second Hole through phantom
29 Target volume
30 Aluminum Box
31 Adjustable Platen
32 Platen Base
33 Phantom support member
34 Assembly base member
35 Controller support fixture
36 Sensor wire
100 Dynamic thorax phantom, general
200 Scanner
201 Scanner bed

DETAILED DESCRIPTION OF THE PREFFERRED EMBODIMENT

The preferred embodiment of the dynamic thorax phantom (generally designated 100 in the Figures) comprises four sub-component systems: tissue equivalent phantom 20 and tissue equivalent rod 21; motion actuator assembly (generally designated 22 in the Figures); motion controller assembly (generally designated 23 in the Figures), which includes controllers, drivers and electronics; and personal computer interface and software (generally indicated as 26 in the Figures).

In the preferred embodiment of the invention, the thorax phantom 20 is approximately 15 cm in longitudinal length, 30 cm wide and 20 cm high. It includes pseudo anthropomorphic, tissue equivalent lungs and spine. Two holes 27 and 28 run longitudinally through the phantom, one (27) parallel to the bottom and side surfaces the other (28) off angle in both directions. A tissue equivalent rod 21*a* and 21*b*, having material densities the same as that of the surrounding phantom 20, are placed within the holes 27 and 28, respectively. Each tissue equivalent rod 21*a* and 21*b* preferably "slip fits" within its respective hole 27 and 28, and moves freely only in a linear and rotation manner within its hole 27 and 28. Within the tissue equivalent rod 21 is preferably a target volume 29 of different density from the density of the tissue equivalent rod 21. The target volume 29 is designed to simulate, for example, a tumor that is to be detected within the phantom 20.

In the preferred embodiment of the invention a detector member 17 is embedded within the target volume 29. The detector member 17 can be of various radiation detectors or sensors, such as MOSFET, TLD, ion chamber or film. In the preferred embodiment of the invention the target volume 29 and detector member 17 are inside of a rod insert 18, which is made of the same material as the tissue equivalent rod 21. A slip fit hole 25 is provided in the tissue equivalent rod 21 to receive the rod insert 18. The rod insert 18 is shaped and sized such that, when it is inserted fully into the hole 25 in the Tissue equivalent rod 21, the hole in the rod is substantially completely filled by the rod insert 18 and the outer surface of the rod-and-insert assembly is continuous and right circular. A hole 24 may be provided in the target volume 29 and the rod insert 18 to receive the detector member 17, and a small groove 19 may be provided in the surface of the Tissue equivalent rod 21 21 to allow connection of a sensor wire 36 to the detector member 17. It will be understood that the device constructed in accordance with the above description allows for various types of detector members 17 inside of any particular rod insert 18. It will also be understood that the device constructed in accordance with the above description allows different rod inserts 18, each having, for example different types (e.g., density variations) of target volumes 29, to be used interchangeably within a Tissue equivalent rod 21, and, accordingly, that such differing target volume-insert-rod combinations can be used interchangeably within a phantom 20.

The motion actuator 22 facilitate two superimposed motions (linear and rotational) that can be simultaneously controlled. This sub-system consists of a stepper motor 3, which converts rotational motion to linear by means of an internal rotating nut (not shown) and an acme screw 4. The acme screw 4, which travels in linear fashion thru the motor 3, is connected to a solid plastic rod 1, which travels thru a slotted cylinder 2. This slot is fitted to receive a locking pin 5, which is fastened to the rod 1 and prohibits the plastic rod 1 from rotating within the cylinder 2, but allows for free linear travel. This lock 5 pin also serves as the trigger mechanism for the linear travel limit switch 15. The slotted cylinder 2 and linear travel mechanism is rotated by means of a second rotational stepper motor via synchronized timing belt 12 and gear (10 and 11) assembly. A precision gear head 13 is used to reduce rotational speed and increase resolution of the rotating linear actuator. Both motors (3 and 14) are electronically controlled to perform coordinated simultaneous motions based on prescribed requirements. The plastic rod 1 is then attached by mechanical means to the tissue equivalent rod 21, which travels thru the phantom 20 thus translating the motion to the Tissue equivalent rod 21 (and target volume 29). The target volume 29 within the tissue equivalent rod 21 can be positioned off center within the rod 21 to add an eccentric or spiral motion to the target or it can be centered thus rotating the target 29 in its own axis.

The mechanical apparatus are housed within an aluminum box 30 that is mounted to an adjustable platen 31. The box 30 can be swiveled up to 60 degrees and the platen 31 can be raised and lowered as well as angled relative to its base 32.

In the preferred embodiment of the invention, in operation, the phantom 20 is secured to a phantom support member 33. The phantom support member 33 is secured in a fixed position to an assembly base member 34, to which a controller support fixture 35 is also attached. The platen base 32 is adjustably secured to the support fixture 35, A motion controller assembly 23 is electrically connected the actuator assembly 22. A computer 26 connected to the controller assembly 23 sends signals to the controller assembly, telling the controller assembly the motion parameters (i.e., range, frequency and direction) that the Tissue equivalent rod 21 is to move. Once the computer 26 has so-instructed the controller assembly 23, the instructions may be stored in the controller memory and the computer 26 can be detached from the controller assembly 23.

The actuator rod 1 moves, (linearly and/or rotationally, in accordance to signals to the actuator assembly 22 from the computer), which in turn causes the tissue equivalent rod 21 (which is attached to the actuator rod 1) to move relative to the phantom 20. It will be appreciated that, in accordance with the present invention, the target volume 29 and detector member 17 within the tissue equivalent rod 21 move together inside of, and relative to, the phantom 20.

By combination of phantom 20 position, rod 21 angle, target volume 29 position, linear motion and rotational motion virtually any motion in three-dimensional space can be simulated.

Figure 11:
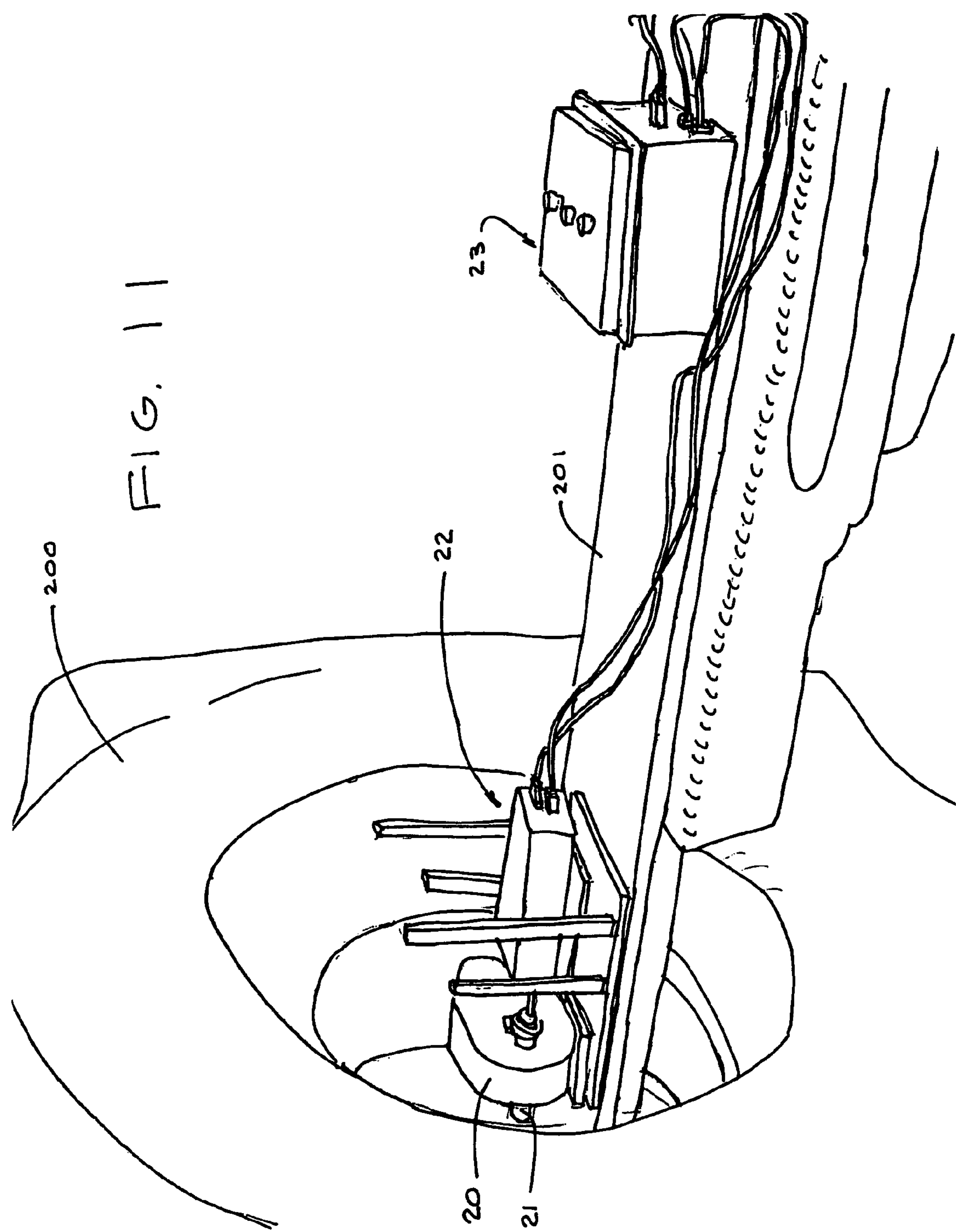
FIG. 11 is a perspective view of the dynamic phantom assembly for radiation therapy constructed in accordance with the present invention, in operating position on a scanner bed.
Figure 12:
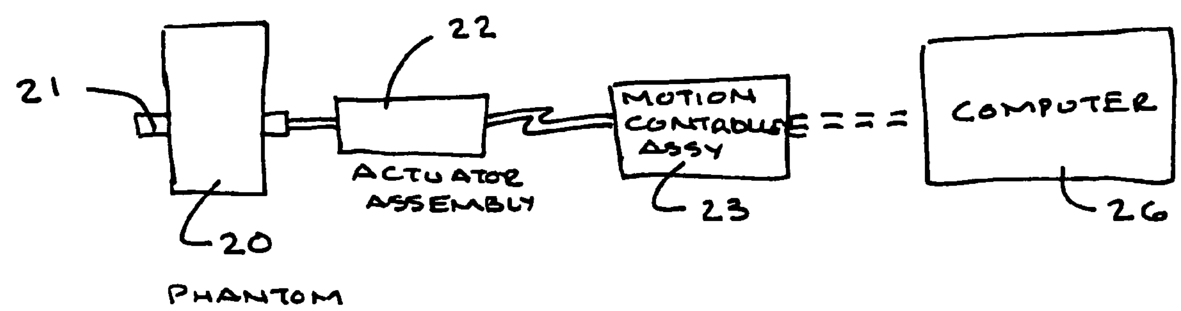
FIG. 12 is a schematic diagram showing the four major sub-component systems of the dynamic phantom assembly.
Figure 13:
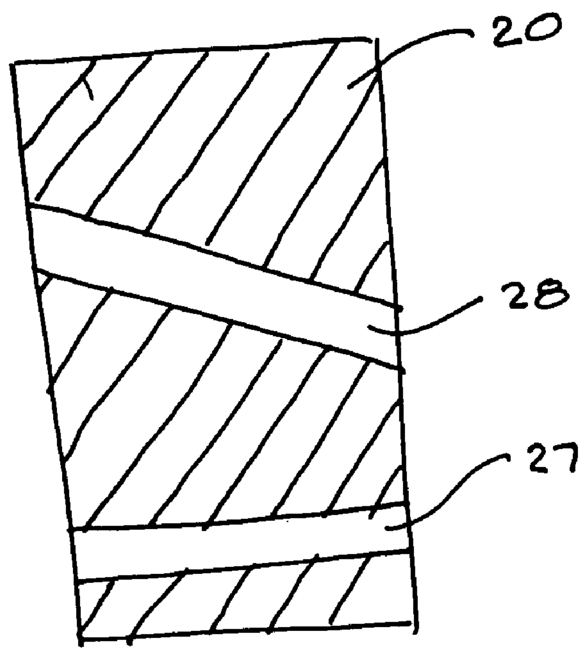
FIG. 13 is a cross-sectional elevation view of the tissue equivalent phantom; and, FIG. 14 is a front elevation view of the tissue equivalent phantom
Figure 14:
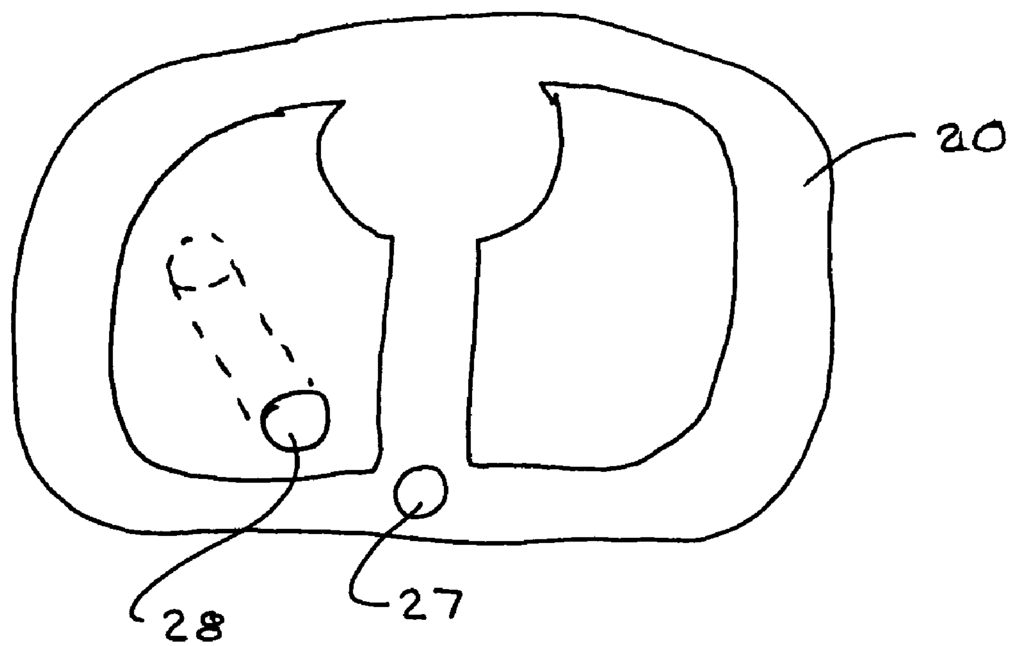

Referring to FIG. 11, in operation the dynamic thorax phantom assembly 100 is placed on the bed 201 of a scanner 200. Power to the dynamic thorax phantom assembly 100 is turned on, and the Tissue equivalent rod 21 moves, according to pre-programmed motion instructions from the motion controller 23. The (typically cyclical) movement of the actuator rod 1, causes like movement of the Tissue equivalent rod 21, the target volume 29 and the detector member 17 relative to the phantom 20. With the dynamic thorax phantom assembly and the bed 201 of the scanner 200 positioned within the scanner, the scanner is operated causing the scanner beam to pass through the stationary phantom 20 to the moving target volume 29 and detector member 17. The dosage of radiation received by the detector member 17 can thereby be recorded, measured and/or verified.

In a modified embodiment of the present invention, the detector member 29 is omitted, and the rod insert 18 surrounds only a target volume 29. This configuration of the invention may be used when it is desired to assess the scanner's (200) ability to resolve the image of moving object.

DETAILS OF THE MECHANICAL DESIGN OF THE ACTUATOR

It will be understood that, in accordance with the present invention, an actuator rod connected to a movable component of a phantom assembly performs a coordinated, controlled linear and rotational motion.

In the preferred embodiment of the invention, the actuator rod 1 is supported and guided in linear direction in the actuator cylinder 2. The rod 1 is at one end attached to the movable phantom component and on the other end to an acme screw 4, which is running inside a stepper motor 3 with a rotating acme nut (not shown). The rotation of the stepper motor is converted into a linear motion of the screw, whereas an anti rotation pin 5 guided in the slot of the cylinder 2 prevents the rod from spinning in the cylinder.

The cylinder 2 is supported in bearings 6 and 7 allowing the rotation of the cylinder with the attached components. The bearings are supported in the bearing plates 8 and 9, which are also the main parts of the actuator overall supporting structure.

The rotational motion is accomplished by using the stepper motor, 14 connected to a low backlash planetary gearhead, 13, and by a low backlash timing belt (synchronous belt) assembly 10,11, 12. The timing belt pulley, 10 is attached to the cylinder, whereas the timing belt pulley 11 is attached to the output shaft of the gear. The Timing belt 12 is connecting the pulleys.

For homing and positioning of the linear motion a limit switch 15 is attached to the cylinder, which is triggered by a plate attached to the anti rotational pin 5. The limit switch 16 which is activated by a cam attached the output shaft of the planetary gear 13, provides the homing for the rotary motion.

The motion of the stepper motors is controlled by a 2-axis motion controller.

While the above description contains many specificities, these should not be construed as limitations on the scope of the invention, but rather as an exemplification of one preferred embodiment thereof. Many other variations are possible, for example:

The tissue equivalent phantom (20) may be of a shape or configuration corresponding to a segment of the human body other than the thorax;

The tissue equivalent phantom (20) may be constructed of any material that has radiation attenuation properties closely matching that of human tissue;

The tissue equivalent rod (21) may be constructed of any material that has radiation attenuation properties that are substantially equal to that of the tissue equivalent phantom (20);

The tissue equivalent phantom (20) may be provided with only a single hole adapted to slidably receive a tissue equivalent rod, or may, alternatively, be provided with multiple such holes;

Direction, speed and/or frequency values may be pre-selected and/or fixed into the motion controller (23) such that the assembly can work (at said pre-selected or fixed conditions) without interfacing with a computer (26).

The tissue equivalent rod (21) may be provided without a target volume, and may, instead, be provided with a radiation-sensitive film, or other radiation detecting material, embedded therein; and, The form of the "radiation" for which the tissue equivalent members have attenuation properties substantially equivalent to that of human tissue, and for which the detector member is capable of detecting, is preferably "X-ray" radiation; however, modified embodiments of the invention within the scope of this invention include tissue equivalent members and detector member(s) that are adapted to be subjected to ultrasonic vibrations and/or magnetic resonance-inducing radio waves (i.e., rather than X-ray radiation), and, the tissue equivalent member are constructed of materials that have ultrasonic vibration attenuation or MRI frequency radio wave attenuation properties, respectively, that are substantially equal to that of human tissue, and the detector member is sensitive to ultrasonic vibration or MRI frequency radio waves, respectively.

Accordingly, the scope of the invention should be determined not by the embodiment illustrated, but by the appended claims and their legal equivalents.

What is claimed is:

1. A dynamic phantom device comprising:

a tissue equivalent first member (20);

a tissue equivalent second member (21); and, means for moving said tissue equivalent second member (21) relative to said tissue equivalent first member (20).

2. The device according to claim 1, wherein said tissue equivalent first member (20) comprises a first opening (28), said first opening being adapted to slidably receive said tissue equivalent second member (21);

and wherein said tissue equivalent second member (21) is disposed within said first opening (28).

3. The device according to claim 2, wherein said tissue equivalent second member (21) is an elongate circular rod having a first end and a second end;

and wherein said means for moving said tissue equivalent second member relative to said tissue equivalent first member comprises a motion actuator (22) and a connector member (1), said connector member (1) being attached to said first end of said elongate rod, and said connector member (1) being attached to said motion actuator (22).

4. The device according to claim 3, further comprising a radiation detector member (17), said radiation detector member (17) being disposed within said tissue equivalent second member (21).

5. The device according to claim 4, further comprising a rod insert member (18), and said second tissue equivalent member (21) having a recess (25) therein adapted to receive and slip fit with said rod insert member (18);

and wherein said radiation detector member (17) is disposed within said rod insert member (18), and said rod insert member (18) is disposed within said recess (25) in said second tissue equivalent member (21).

6. The device according to claim 5, wherein said rod insert member (18) is sized and shaped such that when said rod insert member (18) is disposed within said recess (25) in said second tissue equivalent member (21) said recess (25) is substantially completely filled by said rod insert member (21).

7. The device according to claim 6, further comprising a radiation target member (29) disposed within said elongate rod, and wherein said radiation detector member (17) is disposed within said radiation target member (29) within rod insert member 18.

8. The device according to claim 7, wherein said tissue equivalent first member (20) is constructed of a material having a first material radiation attenuation value;

said tissue equivalent second member (21) is constructed of a material having a second material radiation attenuation value;

and said radiation target member (29) is constructed of a material having a target material radiation attenuation value;

and wherein said target material radiation value is different from said second material radiation attenuation value.

9. The device according to claim 8, wherein said motion actuator (22) comprises a first motor (3) in mechanical communication with said connector member (1), whereby said first motor (3) may induce linear motion in said connector member (1) in a direction parallel to a connector member axis.

10. The device according to claim 9, wherein said motion actuator (22) comprises a second motor (14) in mechanical communication with said connector member (1), whereby said second motor (14) may induce rotational motion in said connector member (1) in a plane perpendicular to said connector member axis.

11. The device according to claim 10, further comprising a motion controller (23) in electrical communication with said motion actuator (22).

12. The device according to claim 11, wherein said tissue equivalent first member is (20) in the shape and size of a human thorax segment, said human thorax segment having a thorax axis extending between a thorax first surface and a thorax second surface.

13. The device according to claim 12, wherein said first opening (28) in said tissue equivalent first member (20) extends continuously between said thorax first surface and said thorax second surface, and wherein said first opening (28) in said tissue equivalent first member has a first opening longitudinal axis, said first opening longitudinal axis being oblique with respect to said thorax axis.

14. The device according to claim 13, wherein said tissue equivalent first member (20) further comprises a second opening (27), said second opening (27) extending continuously between said thorax first surface and said thorax second surface, said second opening (27) having a second opening longitudinal axis, said second opening longitudinal axis being parallel to said thorax axis.

15. The device according to claim 14, further comprising a first support member (33) and means for fixedly securing said tissue equivalent first member (20) to said first support member (33);

a second support member (35) fixedly secured to said first support member (33);

and a motion actuator mount member (32) adjustably connected to said second support member (35);

and wherein said motion actuator (22) is mechanically connected to said motion actuator mount member (32).

16. The device according to claim 15, wherein a material of construction of said tissue equivalent first member and a material of construction of said tissue equivalent second member are both of the same radiation attenuation value; and, wherein said first material radiation attenuation value and said second material radiation attenuation value are substantially equal.

17. The device according to claim 16, wherein said rod insert member is constructed of a material having a rod insert material radiation attenuation value, and wherein said rod insert material radiation attenuation value and said second material radiation attenuation value are substantially equal.

18. The device according to claim 3, wherein said tissue equivalent first member (20) is constructed of a material that has X-Ray attenuation properties substantially equivalent to that of a human tissue;

and said tissue equivalent second member is constructed of a material that has X-Ray attenuation properties substantially equivalent to that said tissue equivalent first member (20);

and further comprising an X-Ray radiation detection member (17), said X-Ray radiation detector member (17) being disposed within said tissue equivalent second member (21);

and means for moving said tissue equivalent second member (21) relative to said tissue equivalent first member (20).

19. The device according to claim 3, wherein said tissue equivalent first member (20) is constructed of a material that has ultrasonic vibration attenuation properties substantially equivalent to that of a human tissue;

and said tissue equivalent second member is constructed of a material that has ultrasonic vibration attenuation properties substantially equivalent to that said tissue equivalent first member (20);

and further comprising an ultrasonic vibration detection member (17), said ultrasonic vibration detector member (17) being disposed within said tissue equivalent second member (21);

and means for moving said tissue equivalent second member (21) relative to said tissue equivalent first member (20).

20. The device according to claim 3, wherein said tissue equivalent first member (20) is constructed of a material that has nuclear magnetic resonance properties substantially equivalent to that of a human tissue;

and said tissue equivalent second member is constructed of a material that has nuclear magnetic resonance properties substantially equivalent to that said tissue equivalent first member (20);

and further comprising a target member (29), said target member having nuclear magnetic resonance properties that at different from those of said tissue equivalent second member (21).

* * * * *